(12) United States Patent
Modi

(10) Patent No.: US 11,383,055 B2
(45) Date of Patent: Jul. 12, 2022

(54) PATIENT VENTILATOR SYSTEM AND METHOD

(71) Applicant: GE Precision Healthcare LLC, Wauwatosa, WI (US)

(72) Inventor: Chetankumar Amrutlal Modi, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 676 days.

(21) Appl. No.: 16/366,654

(22) Filed: Mar. 27, 2019

(65) Prior Publication Data

US 2020/0306472 A1    Oct. 1, 2020

(51) Int. Cl.
*A61M 16/00*  (2006.01)
*A61M 16/10*  (2006.01)

(52) U.S. Cl.
CPC ...... *A61M 16/024* (2017.08); *A61M 16/0003* (2014.02); *A61M 16/0069* (2014.02); *A61M 16/1065* (2014.02); *A61M 2016/103* (2013.01)

(58) Field of Classification Search
CPC ............ A61M 16/024; A61M 16/0003; A61M 16/0069; A61M 16/1065; A61M 2016/103
See application file for complete search history.

(56) References Cited

U.S. PATENT DOCUMENTS

| | | | | |
|---|---|---|---|---|
| 5,549,106 | A  * | 8/1996 | Gruenke | A61M 16/026 |
| | | | | 128/204.23 |
| 9,802,015 | B2 * | 10/2017 | Virr | A61M 16/0875 |
| 2018/0093063 | A1 | 4/2018 | Rajan et al. | |
| 2018/0221606 | A1 | 8/2018 | Brandt et al. | |
| 2018/0280654 | A1 * | 10/2018 | Borrello | A61M 16/12 |
| 2019/0038858 | A1 * | 2/2019 | Ahmad | A61M 16/201 |
| 2020/0360635 | A1 * | 11/2020 | Chaudhry | A61M 16/209 |
| 2021/0379308 | A1 * | 12/2021 | Tumu | A61M 16/0066 |

OTHER PUBLICATIONS

Dräger Medical AG & Co. KG, Zeus Anesthetic Workstation Service Manual, pp. 1-179.

* cited by examiner

*Primary Examiner* — Steven O Douglas
(74) *Attorney, Agent, or Firm* — Andrus Intellectual Property Law, LLP

(57) ABSTRACT

A patient ventilator system includes a patient delivery circuit having an inspiratory section that delivers an inspiratory gas flow to a patient and an expiratory section that receives expiratory gas flow from the patient, wherein a bidirectional blower motor drives the inspiratory gas flow in the inspiratory section and controls the expiratory gas flow in the expiratory section. A flow sensor measures gas flow rate between the bidirectional blower motor and the patient delivery circuit. A four quadrant controller is configured to control speed and direction of the bi-directional blower motor based on the measured flow rate so as to effectuate ventilation for the patient.

20 Claims, 3 Drawing Sheets

PATIENT VENTILATOR SYSTEM AND METHOD

BACKGROUND

The present disclosure generally relates to patient ventilator systems, and more particularly to ventilation systems incorporating a bi-directional blower motor as a ventilation drive and methods and control systems for operating such a bi-directional blower motor.

Conventional ventilator systems have a patient delivery circuit comprising an expiratory section and an inspiratory section. The patient delivery circuit is used for delivering gases comprising oxygen and other gases optionally infused with an inhalational anesthetic agent to a patient, such as under positive end-expiratory pressure, and for providing ventilation control to the patient. As used herein, the term "ventilation" refers to a process of providing mechanical assistance to a patient for breathing. As used herein, "breathing gases" refer to gases inhaled by the patient from the patient delivery circuit and gases exhaled by the patient into the patient delivery circuit during breathing. Also, as used herein, "inspiratory gas flow" refers to gases transported along the inspiratory section of the patient delivery circuit, which are inhaled or inspired by a patient from the inspiratory section of the patient delivery circuit and gases bypassing patient inhalation and transported directly into the expiratory section of the patient delivery circuit. Also, as used herein, "expiratory section gases" refer to gases that are exhaled or expired by the patient into the expiratory section of the patient delivery circuit and gases bypassing inhalation and transported directly into the expiratory section from the inspiratory section which are not exhaled by the patient, both of which are transported along the expiratory section.

Conventional anesthesia delivery systems are typically configured as bellows systems where inspiratory and expiratory gases are driven by a bellow. A conventional bellows system is a complex mechanical system that introduces cost. Typically, a ventilation drive provides ventilation gases into a chamber surrounding the bellow, which moves the bellow. The ventilation drive typically utilizes pressurized air, and typically the pressurized ventilation gases. The ventilation gases used to drive the bellows are not delivered to the patient, and thus there is a cost associated with the gas supply for operating the bellows.

A conventional patient ventilator system comprises a circulating loop with a flow proportional valve in the expiratory section for restricting the flow of breathing gases, thereby creating a back pressure upstream of the flow proportional valve. The back pressure results in the creation of a positive end-expiratory pressure (PEEP) in the lungs of the patient by restricting the flow of breathing gases upstream of the flow proportional valve. A typical PEEP pressure between about 2 cm water ($H_2O$) and about 10 cm $H_2O$ is required to be maintained in the lungs of a patient to keep the lungs open and to prevent the lungs from collapsing during or at the end of expiration, or to assist with alveolar inflation during the ventilation of the patient. PEEP helps to keep the alveoli open and reduces pulmonary edema, which is ingress of liquid from the capillaries into the alveoli. Without application of PEEP, the pressure inside the lungs at the end of expiration is typically about 0 cm $H_2O$ (atmospheric pressure).

In existing patient ventilator systems, a flow proportional valve functions to create a positive end-expiratory pressure in an anesthesia circulating loop, which is referred to as a positive end-expiratory pressure (PEEP) valve. A PEEP valve is used in a conventional anesthesia circulating loop to maintain a pressure of about 2 cm $H_2O$ to about 4 cm $H_2O$, or more, above atmospheric pressure within the patient's lungs. The PEEP valve is typically positioned on an expiratory section, with the exact location selected by a manufacturer of the patient delivery circuit. Various conventional PEEP valve configurations are known in the art for setting and regulating PEEP pressures.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a patient ventilator system includes a patient delivery circuit having an inspiratory section that delivers an inspiratory gas flow to a patient and an expiratory section that receives expiratory gas flow from the patient, wherein a bidirectional blower motor drives the inspiratory gas flow in the inspiratory section and controls the expiratory gas flow in the expiratory section. A flow sensor measures gas flow rate between the bidirectional blower motor and the patient delivery circuit. A four quadrant controller is configured to control speed and direction of the bi-directional blower motor based on the measured flow rate so as to effectuate ventilation for the patient.

One embodiment of a method for driving ventilation of a patient includes controlling, with a four quadrant (FQ) controller, a bi-directional blower motor in the forward direction at a forward speed to effectuate inspiratory gas flow through an inspiratory section of a patient delivery circuit to a patient, and controlling, with the FQ controller, the bi-directional blower motor in a reverse direction at a reverse speed to effectuate expiratory gas flow from the patient through an expiratory section of the patient delivery circuit.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Most available patient ventilator systems use a pressurized gas source along with a flow and PEEP control valve to drive bellows for delivering mechanical ventilation to a patient. The pressurized gas that is used for moving the bellows in order to drive an inspiratory ventilation phase is then released to atmosphere. This drive gas is typically oxygen ($O_2$) because of its availability and because it is a mandatory gas for patient ventilation. This drive gas consumed for driving the bellows adds additional cost of ownership of a patient ventilator system, costing several thousand dollars or more per year.

Figure 1:
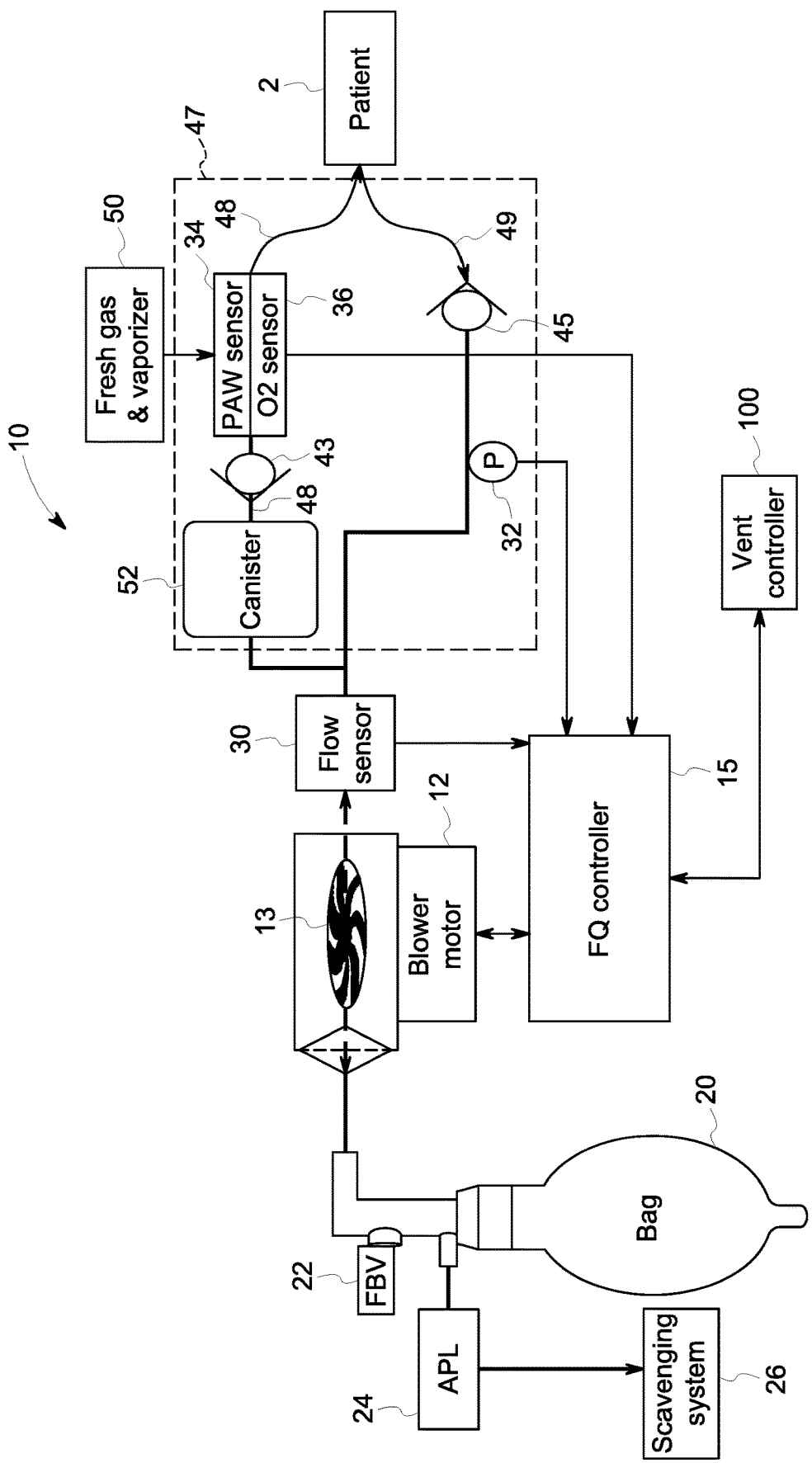
FIG. 1 illustrates an exemplary embodiment of a patient ventilator system comprising a bi-directional blower motor controlled by a four quadrant controller.
Figure 2:
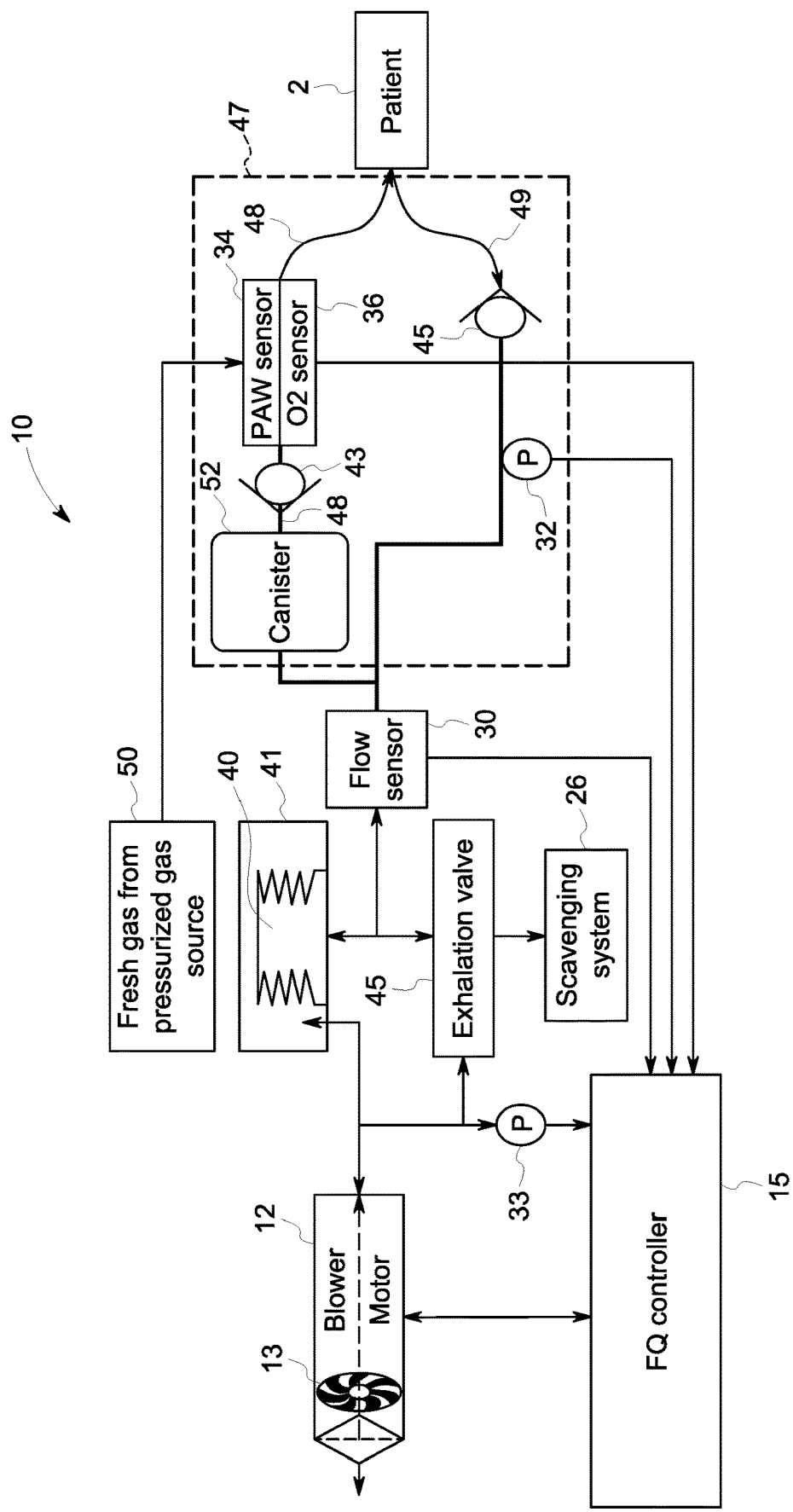
FIG. 2 illustrates another exemplary embodiment of a patient ventilator system comprising a bi-directional blower motor controlled by a four quadrant controller.

Instead of a pressurized gas source, the disclosed methods and systems utilize a bi-directional blower motor to drive both inspiratory gas flow and expiratory gas flow in a patient delivery circuit. A four quadrant (FQ) controller is configured to control the bi-directional blower motor so as to effectuate the inspiratory and expiratory gas flows in the patient delivery circuit. FIG. 1 illustrates one embodiment of such a patient ventilator system 10, which is a bellowless patient ventilator drive (i.e., does not contain any bellow) using a bi-directional blower motor 12 controlled by a FQ controller 15. FIG. 2 illustrates another embodiment, where the bi-directional blower motor 12 and FQ controller 15 drive operation of the bellow 40 in order to effectuate the inspiratory and expiratory gas flows to the patient 2. In both exemplary embodiments, the FQ controller controls the speed, or revolutions per minute (RPM), of the motor in one of four modes—a forward drive mode, a forward braking mode, a reverse drive mode, and a revers braking mode—to deliver precise mechanical ventilation. In some examples, the FQ controller may collect energy during the "braking" modes, thereby using regenerative energy from the bi-directional blower motor.

The bi-directional blower motor is controllable to force gas toward the patient (referred to herein as a "forward direction"), and to draw gas away from the patient (referred to herein as a "reverse direction"). Accordingly, in the forward direction, inspiratory gas flow is provided from the blower motor 12 to the inspiratory section 48, thus driving the inspiratory ventilation to the patient 2. The blower motor 12 operates in a reverse direction to draw expiratory gas flow from the patient 2 into the expiratory section 49 of the patient delivery circuit 47 and into the blower motor 12. With reference to FIG. 1, the blower motor 12 includes a spindle 13, or fan, driven into a forward rotation in order to drive the inspiratory gas flow and provide a given inspiratory pressure, and is rotated in a reverse rotational direction in order to effectuate the expiratory gas flow and a designated expiratory pressure. To provide one example, the bi-directional blower motor may be a brushless DC (BLDC) motor that can run up to 100,000 RPM to generate the pressurized airflow up to 150 SLPM and a pressure up to 110 cm $H_2O$.

Accordingly, the blower motor drives patient ventilation utilizing the surrounding air in the atmosphere rather than requiring a pressurized gas source to drive the ventilation. This simplifies the design of the patient ventilator system 10 by eliminating several traditional elements associated with conventional ventilator drive systems, such as elimination of a pressure regulator, an inspiratory flow control valve, a pressure switch, a PEEP control valve, a safety valve, a mechanical over pressure valve (MLPV), a free breathing valve, and a pop-off valve. Moreover, in the bellowless embodiment of FIG. 1, the bellow assembly is eliminated entirely, as is the conventional bag-and-vent switch for switching between mechanical ventilation and manual bag-compression ventilation. Thereby, the disclosed systems and methods are simpler and more reliable, are easier to maintain, and save costs by eliminating the use of pressurized gas.

In the embodiment of FIG. 1, the blower motor 12 and FQ controller 15 are utilized instead of a traditional ventilator engine and control valve. The blower motor 12 and FQ controller 15 directly drive and control the breathing gas flow and pressure in the patient delivery circuit 47. The gas flow and pressure are controlled by operating the blower motor 12 in reciprocating directions such that the blower motor 12 directly delivers the inspiratory gases to the inspiratory section 48 of the patient delivery circuit 47 and receives the expiratory gas flow from the expiratory gas section 49 of the patient delivery circuit 47. Thereby, the blower motor 12 directly delivers the breathing gases at a desired flow rate and pressure for each of the inspiratory and expiratory phases of ventilation. During the expiratory phase, the blower motor 12 may be controlled to run at a reduced RPM compared to the inspiratory phase so as to control PEEP. The measured expiratory pressure can be utilized by the FQ controller 15, such as from the pressure sensor 32 described below, so as to deliver PEEP to the patient, where the FQ controller 15 controls the blower motor 12 at a reduced RPM such that the expiratory pressure does not fall below a preset PEEP maintenance pressure.

In the embodiment of FIG. 1, a reservoir bag 20 serves as a reservoir and receives the expiratory gas flow and volume from the expiratory section 49 of the patient delivery circuit 47. During the expiratory ventilation phase, the exhalation valve 45, which is a one way valve, opens to allow gas to flow from the patient 2 through the expiration section 49 to the blower motor 12. The expiratory gas flow travels from the patient delivery circuit 47 through a portion of the blower motor 12 comprising the spindle 13 and to the reservoir bag 20. An adjustable pressure limit (APL) valve 24 acts to limit pressure inside the reservoir bag 20 during mechanical ventilation. To provide one example, the reservoir bag may be configured to contain 1.5 liters of gas at 3 $cmH_2O$, and the APL valve 24 may limit the pressure inside the reservoir bag 20 to 5 $cmH_2O$ of pressure. The output of the APL valve 24 is provided to the scavenging system 26 so as to remove any anesthetic agents or other designated substances from the exhalation gases before releasing them to the surrounding atmosphere.

The blower motor 12 is then controlled to reverse the direction of airflow in order to effectuate the transition from the expiratory phase where gas is driven from the patient 2 to the reservoir bag 20, to the inspiratory phase where gas is driven from the reservoir bag 20 toward the patient 2 via the inspiratory section 48. The reservoir bag 20 is thereby deflated. A free breathing valve (FBV) 22 is positioned between the reservoir bag 20 and the blower motor 12 which opens at a predefined negative pressure so as to allow intake of atmospheric gas to the blower motor 12 during the inspiratory ventilation phase. For example, the FBV 22 may be configured to allow atmospheric gas to enter the system at a negative pressure of 5 cmH2O.

The inspiratory gas flow is delivered from the blower motor 12 through the $CO_2$ absorber 52 to the inspiratory section 48 of the patient delivery circuit 47. The $CO_2$ absorber 52 removes $CO_2$ from the exhalation gases provided from the bag 20. The inhalation valve 43, which is a one way valve, opens at the initiation of the inhalation phase in order to permit gas to flow into the inspiratory section 48 to the patient 2. In embodiments where anesthesia is provided to the patient, a gas source 50 and vaporizer may provide anesthetic agent into the inhalation gas flow.

Sensors measure conditions within the patient delivery circuit 47. Several sensors in the inspiratory section 48 may provide measurements to the FQ controller 15 so as to enable effective ventilation control. A mean airway pressure (PAW) sensor 34 may be configured to measure a mean inspiratory pressure in the inspiratory section 48, and the FQ controller 15 may be configured to control the speed of the blower motor 12 in order to achieve a predefined instantaneous inspiratory pressure and/or mean inspiratory pressure. An $O_2$ sensor 36 may also be configured to measure an oxygen concentration in the inspiratory section 48. The $O_2$ sensor may be utilized, for example, to control the Fresh Gas flow so as to control oxygen delivery to the patient 2. A pressure sensor 32 is configured to measure a pressure in the delivery circuit 47. For example, the pressure sensor 32 may be configured to measure expiratory pressure of the expiratory section 49 during the expiratory ventilation phase. The pressure sensor 32 may also be utilized to mitigate possible patient safety risks in a case where the PAW sensor fails, thus the pressure measurements from the pressure sensor 32 may also be utilized as a backup for the PAW sensor during the inspiratory phase.

A flow sensor 30 is positioned between the bi-directional blower motor 12 and the patient delivery circuit 47 to measure a gas flow rate generated by the blower motor 12. The flow sensor 30 is configured to measure the flow rate in both directions, and to provide the flow measurements to the FQ controller 15. Thus, the flow sensor 30 may be positioned adjacent to the blower spindle 13. The FQ controller 15 controls the RPM of the blower motor 12 accordingly so as to provide the predefined expiratory and inspiratory flow according to ventilation parameter settings, such as may be instructed by the ventilation controller 100 calculating desired flow rates, pressures, and other ventilation values. For example, the FQ controller 15 may include software providing a feed-forward proportional-integral-derivative control loop along with the four quadrant motor control strategy, to control the RPM of the blower motor based on patient ventilation parameter settings.

The speed of the blower motor 12 is continuously controlled by the FQ controller 15, which also controls the direction of the blower. The FQ controller 15 can apply torque in the same vector polarity (direction) in which the motor is running, and can also apply a torque in the opposite direction to the motor's rotational velocity in order to decelerate, or "brake," the motor in a fast and controlled fashion. The FQ controller 15 operates in a four quadrant strategy to provide for different control modes for the blower motor 12 including:
  Mode 1. Motor going clockwise, controller applying clockwise drive torque (e.g., a "forward drive mode")
  Mode 2. Motor going clockwise, controller applying anti-clockwise drive torque (e.g., a "forward braking mode")
  Mode 3. Motor going anti-clockwise, controller applying anti-clockwise drive torque (e.g., a "reverse drive mode")
  Mode 4. Motor going anti-clockwise, controller applying clockwise drive torque (e.g., a "reverse braking mode")
The anti-directional, or "braking," drive modes can quickly and accurately decelerate the blower motor 12 over a specific ramp. Operation in a drive mode then initiates rotation in an equally controlled way. This control strategy also allows for regenerative braking. As the motor is slowed down, the kinetic energy of the rotational motion transfers into electric energy, which can be stored and utilized. For example, the stored energy may be utilized to apply additional torque initiate rotation in the opposite direction. Thereby, the FQ controller 15 may be configured to utilize regenerated energy collected during the deceleration phase of one breath to accelerate the motor to initiate the next breath. For example, the FQ controller 15 may have a battery bank or capacitor bank for storing energy created during the deceleration modes, which may then be used to provide a power boost to initiate rotation of the blower motor 12 in the opposite direction. Thereby, the energy for the battery bank is utilized to reduce the work of breathing for the patient 2 and/or reduces the overall energy consumption of the system 10.

In the embodiment of FIG. 1, the blower motor 12 comes in contact with the expiratory gases from the patient 2. Thus, the portions of the blower motor that contact patient expiratory gases must meet cleaning and disinfection requirements. In one example, the blower motor 12 may include a detachable spindle 13 from the rest of the blower motor 12, wherein the detachable spindle 13 can be cleaned and disinfected. Alternatively, the blower motor 12 may be sealed system up to a certain water pressure using magnetic fluid, for example.

FIG. 2 depicts a different embodiment where the patient ventilator system 10 incorporates a conventional bellow system, including a bellow 40 in a pressure chamber 41. The bi-directional blower motor 12 controlled by the FQ controller 15 is coupled to the pressure chamber 41 and configured to control pressure therein so as to effectuate patient ventilation. Thus, the blower motor 12 does not directly contact the breathing gases delivered to the patient, and thus does not need to meet the same cleaning and disinfection requirements. In the embodiment of FIG. 2, the drive gas used to drive the patient respiration is completely isolated from the patient gas. The bi-directional blower motor 12 is coupled to the pressure chamber 41 and drives the gas flow and pressure in the patient delivery circuit 47 by controlling pressure in the pressure chamber 41. The patient delivery circuit 47 includes inspiratory and expiratory sections 48 and 49 that facilitate patient ventilation as described above.

The pressurized gas from the blower 12, 13 is used to apply pressure on the exhalation valve 45 and on the bellow 40. The blower motor 12 is controlled to control the inhalation and exhalation gas flows and pressures by generating pressure on the bellow 40, wherein the exhalation valve 45 is configured to set a maximum bias pressure. For example, the exhalation valve may be designed with a bias pressure such that the valve releases gas pressure inside the bellow once that threshold maximum bias pressure is reached. To provide one example, the bias pressure may be in the range of 2-3 cm $H_2O$. The exhalation valve 44 is a pneumatically-driven valve that operates using the pressurized gas from blower motor. The exhalation valve 45 is configured to open when gas pressure inside the bellow is higher than pressure outside the bellow by a predetermined bias pressure. Once the bellow reaches the predetermined bias pressure, the exhalation valve 45 opens and releases gas to the scavenging system 26. Input from a pressure sensor 33 may be positioned on the drive gas path near the exhalation valve 45 to monitor pressure and to mitigate a possible patient safety risk where PAW sensor 34 failure occurs.

During the exhalation phase, the drive gas pushed into the pressure chamber 41 by the blower motor 12 is released from the pressure chamber 41 back through the blower motor 12, which operates to control the gas flow out of the pressure chamber 41. Expansion of the bellow 40 results, which pulls gases away from the patient via the expiratory section 49 of the patient delivery circuit 47, as is customary. The drive gas exiting the blower motor 12 is released to atmosphere and the expiratory gas flow from the patient 2 goes into the bellow 40.

Figure 3:
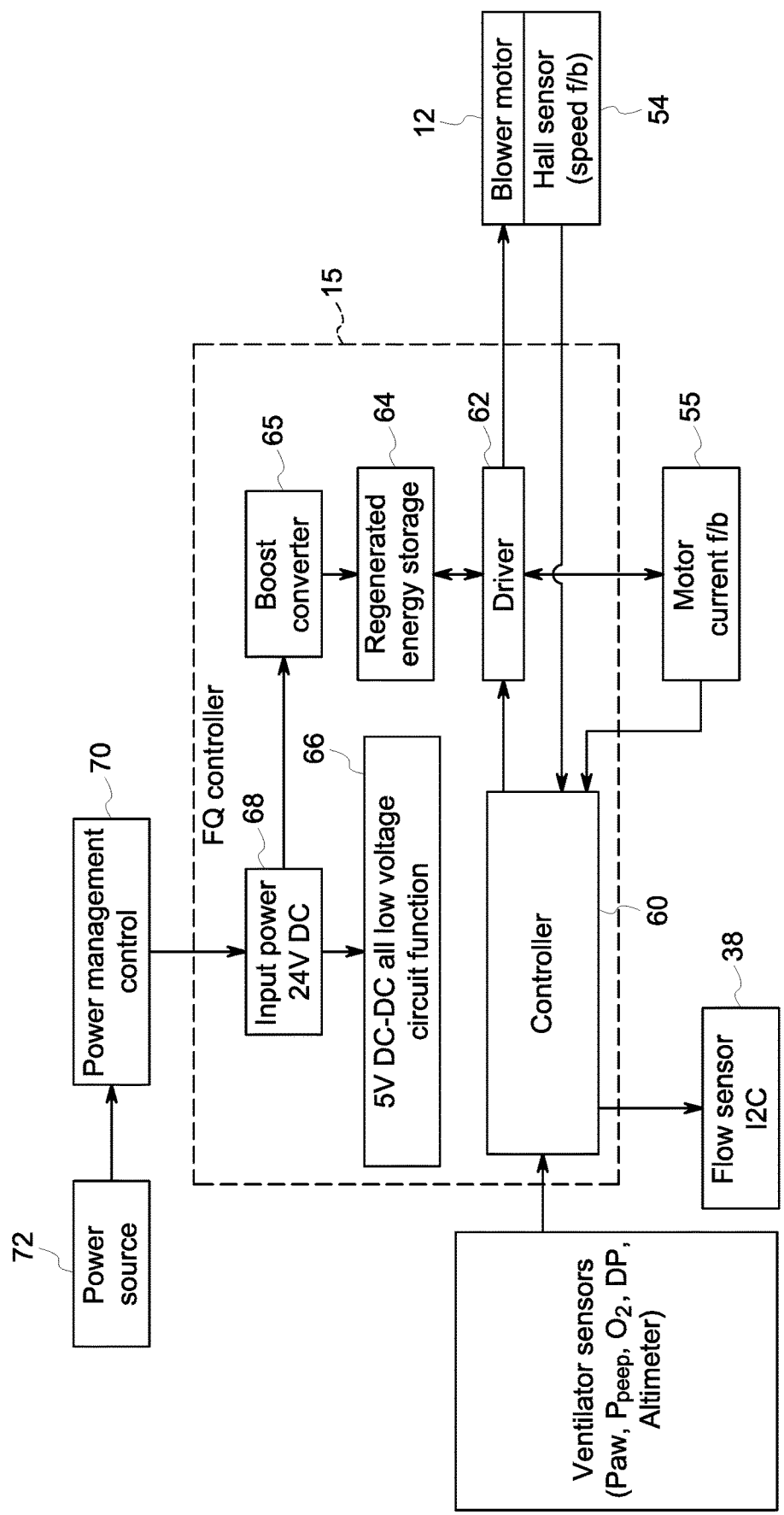
FIG. 3 is a schematic diagram exemplifying one embodiment of a controller system architecture for a patient ventilator system drive using a bi-directional blower motor and a four quadrant controller.

FIG. 3 is a schematic drawing depicting certain aspects of the control system architecture for one embodiment of the disclosed patient ventilator system 10. The FQ controller 15 includes one or more controllers 60, such as one or more microcontrollers, controlling a driver 62 that drives the blower motor 12. The driver 62 is configured to apply a torque in order to influence motion of the blower motor 12, which may be a clockwise drive torque or an anti-clockwise drive torque in order to control the RPM of the blower motor 12. A speed sensor 54, such as a Hall effect sensor, provides feedback to the controller 60 for controlling speed of the blower motor 12. A current sensor 55 may also be associated with the blower motor 12 in order to sense a current draw of the motor 12 and provide such information to the driver 62 and/or the controller 60. The controller 60 further receives measurements from flow sensor 38 and one or more ventilator sensors as described above, such as PAW sensor 34, $O_2$ sensor 36, pressure sensor 32 or 33, etc. The controller determines the appropriate speed and direction of the blower motor 12 needed to effectuate the ventilation parameters (e.g., determined by ventilation controller 100), and controls the driver 62 accordingly to effectuate the appropriate control mode and apply the appropriate torque.

One exemplary controller 60 is the Texas Instrument TMS320F2806x Piccolo™ Microcontroller, which has a programmable Control Law Accelerator (CLA) module that is specially designed to run fast close loop control and can be configured to provide the fast motor control necessary for the control application disclosed herein. Therefore, the controller 60 may execute software code for controlling the blower motor 12 for controlling the ventilation parameters, which may be determined and/or set by the ventilation controller 100. However, as will be understood by a person having ordinary skill in the art in light of this disclosure, other microcontrollers may be utilized for the FQ controller 15 and provide similar efficacy.

The FQ controller 15 includes power management elements for powering the driver 62 and also for enabling energy regeneration during the regenerative braking modes. For example, the FQ controller includes a regenerated energy storage device or system 64, such as a capacitor bank or a battery bank, a boost converter 65 and a DC power converter 66 that manage the input power from the power input 68. Power is provided to the power input 68 from a power source 72, such as a battery or AC source, which is provided through a power management controller 70.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A patient ventilator system comprising:
   a patient delivery circuit having an inspiratory section that delivers inspiratory gas flow to a patient and an expiratory section that receives expiratory gas flow from the patient;
   a bi-directional blower motor that drives the inspiratory gas flow in the inspiratory section and controls the expiratory gas flow in the expiratory section;
   a flow sensor measuring gas flow rate between the bi-directional blower motor and the patient delivery circuit; and
   a four quadrant (FQ) controller configured to control speed and direction of the bi-directional blower motor based on the measured flow rate so as to effectuate ventilation for the patient.

2. The patient ventilator system of claim 1, further comprising a pressure sensor configured to measure expiratory pressure in the expiratory section;
   wherein the FQ controller is further configured to control the speed of the bi-directional blower motor based on the expiratory pressure so as to deliver positive end expiratory pressure (PEEP) to the patient.

3. The patient ventilator system of claim 2, further comprising a mean airway pressure (PAW) sensor configured to measure mean inspiratory pressure in the inspiratory section;
   wherein the FQ controller is further configured to control the speed and/or direction of the bi-directional blower motor based on the mean inspiratory pressure.

4. The patient ventilator system of claim 1, wherein the bi-directional blower motor is directly coupled to the patient delivery circuit such that it delivers the inspiratory gas flow to the inspiratory section and receives the expiratory gas flow from the expiratory section.

5. The patient ventilator system of claim 4, further comprising a reservoir bag that receives and stores expiratory gas from the bi-directional blower motor during an expiratory ventilation phase, and provides the expiratory gas back to the bi-directional blower motor during an inspiratory ventilation phase.

6. The patient ventilator system of claim 5, further comprising a free breathing valve positioned between the reservoir bag and the bi-directional blower motor, wherein the free breathing valve is configured to open at a predefined negative pressure so as to allow intake of atmospheric gas to the bi-directional blower motor during the inspiratory ventilation phase.

7. The patient ventilator system of claim 5, further comprising an adjustable pressure limit valve positioned between the reservoir bag and the bi-directional blower motor, wherein the adjustable pressure limit valve is configured to open at a predefined positive pressure so as to limit pressure inside the reservoir bag during the expiratory ventilation phase.

8. The patient ventilator system of claim 1, further comprising a bellow contained in a pressure chamber;
   wherein the bi-directional blower motor is coupled to the pressure chamber and configured to control pressure therein so as to effectuate the ventilation to the patient.

9. The patient ventilator system of claim 8, further comprising a chamber pressure sensor configured to measure pressure in the pressure chamber, wherein the FQ controller is further configured to control the speed and/or the direction of the bi-directional blower motor based on the pressure in the pressure chamber.

10. The patient ventilator system of claim 9, wherein the speed and the direction of the bi-directional blower motor is controlled to drive the inspiratory gas flow to the patient by increasing pressure in the pressure chamber to deflate the bellow and to control the expiratory gas flow from the patient by decreasing pressure in the pressure chamber to inflate the bellow.

11. The patient ventilator system of claim 8, wherein the flow sensor is positioned to measure flow rate between the bellow and the patient delivery circuit.

12. The patient ventilator system of claim 11, further comprising further comprising a mean airway pressure (PAW) sensor configured to measure mean inspiratory pressure in the inspiratory section;
  wherein the FQ controller is further configured to control the speed and/or direction of the bi-directional blower motor based on the mean inspiratory pressure.

13. A method for driving ventilation of a patient, the method comprising:
  controlling, with a four quadrant (FQ) controller, a bi-directional blower motor in a forward direction at a forward speed to effectuate inspiratory gas flow through an inspiratory section of a patient delivery circuit to a patient; and
  controlling, with the FQ controller, the bi-directional blower motor in a reverse direction at a reverse speed to effectuate expiratory gas flow from the patient through an expiratory section of the patient delivery circuit.

14. The method of claim 13, further comprising, with the FQ controller:
  applying a reverse direction torque on the bi-directional blower motor when it is rotating the forward direction to effectuate a transition from the inspiratory gas flow to the expiratory gas flow; and
  applying a forward direction torque on the bi-directional blower motor when it is rotating the reverse direction to effectuate a transition from the expiratory gas flow to the inspiratory gas flow.

15. The method of claim 13, further comprising:
  measuring a flow rate of gas delivered to the patient delivery circuit with a flow sensor;
  adjusting the forward speed based on the flow rate;
  measuring a flow rate of gas received from the patient delivery circuit with a flow sensor; and
  adjusting the reverse speed based on the flow rate.

16. The method of claim 15, wherein the flow rate is measured adjacent to the bi-directional blower motor.

17. The method of claim 13, further comprising:
  measuring expiratory pressure in the expiratory section with a pressure sensor; and
  wherein the FQ controller controls the speed and/or direction of the bi-directional blower motor based on the expiratory pressure so as to deliver positive end expiratory pressure (PEEP) to the patient.

18. The method of claim 13, wherein the bi-directional blower motor is directly coupled to the patient delivery circuit so as to deliver the inspiratory gas flow to the inspiratory section and receive the expiratory gas flow from the expiratory section.

19. The method of claim 13, wherein the bi-directional blower motor is coupled to a bellow contained in a pressure chamber and configured to control a pressure in the pressure chamber so as to effectuate the inspiratory gas flow and the expiratory gas flow.

20. The method of claim 19, wherein controlling the bi-directional blower motor in the forward direction at the forward speed increases the pressure in the pressure chamber to deflate the bellow so as to effectuate the inspiratory gas flow, and controlling the bi-directional blower motor in the reverse direction at the reverse speed decreases the pressure in the pressure chamber to effectuate the expiratory gas flow.

* * * * *